United States Patent
Serval et al.

(10) Patent No.: US 10,349,733 B2
(45) Date of Patent: Jul. 16, 2019

(54) TOOTHBRUSH SYSTEM WITH SENSORS FOR A DENTAL HYGIENE MONITORING SYSTEM

(71) Applicant: KOLIBREE, Paris (FR)

(72) Inventors: Thomas Serval, Paris (FR); Loic Cessot, Paris (FR); Samuel Landau, Neuilly-sur-Seine (FR)

(73) Assignee: KOLIBREE, Paris (FR)

(*) Notice: Subject to any disclaimer, the term of this patent is extended or adjusted under 35 U.S.C. 154(b) by 437 days.

(21) Appl. No.: 14/900,093

(22) PCT Filed: Apr. 4, 2014

(86) PCT No.: PCT/EP2014/056844
§ 371 (c)(1),
(2) Date: Dec. 18, 2015

(87) PCT Pub. No.: WO2014/202250
PCT Pub. Date: Dec. 24, 2014

(65) Prior Publication Data
US 2016/0143718 A1 May 26, 2016

Related U.S. Application Data

(60) Provisional application No. 61/836,837, filed on Jun. 19, 2013.

(51) Int. Cl.
*A46B 15/00* (2006.01)
*A61C 17/22* (2006.01)

(52) U.S. Cl.
CPC ...... *A46B 15/0004* (2013.01); *A46B 15/0006* (2013.01); *A46B 15/0008* (2013.01);
(Continued)

(58) Field of Classification Search
CPC ............ A46B 15/0002; A46B 15/0004; A46B 15/0006; A46B 15/0008; A46B 15/001;
(Continued)

(56) References Cited

U.S. PATENT DOCUMENTS

| 6,536,068 B1 * | 3/2003 | Yang | A46B 15/0002 |
| | | | 15/105 |
| 6,731,213 B1 * | 5/2004 | Smith | A46B 15/0002 |
| | | | 15/167.1 |

(Continued)

FOREIGN PATENT DOCUMENTS

| CN | 104523000 A | | 4/2015 |
| DE | 10045067 | * | 4/2002 |

(Continued)

OTHER PUBLICATIONS

International Preliminary Report on Patentability for PCT/EP2014/056844 dated Dec. 17, 2015, 11 pages.

(Continued)

*Primary Examiner* — Mark Spisich
(74) *Attorney, Agent, or Firm* — Nixon Peabody LLP

(57) ABSTRACT

Tooth brushing monitoring system is disclosed that includes a toothbrush with sensors and a base station. The sensors record data regarding the quality, quantity and location of brushing and the system can analyze the data to provide feedback on the quality of brushing. This feedback provides motivation for users to increase their brushing habits, leading to a decrease in plaque, tooth decay and gingivitis.

23 Claims, 5 Drawing Sheets

(52) U.S. Cl.
CPC ...... *A46B 15/0012* (2013.01); *A46B 15/0038* (2013.01); *A61C 17/221* (2013.01)

(58) Field of Classification Search
CPC ............ A46B 15/0012; A46B 15/0038; A46B 15/004; A46B 15/0042; A46B 15/0044; A46B 15/0046; A46B 13/00; A46B 13/02; A46B 13/023; A61C 17/00; A61C 17/16; A61C 17/22; A61C 17/221; A61C 17/222; A61C 17/224; A61C 17/225
See application file for complete search history.

(56) References Cited

U.S. PATENT DOCUMENTS

| | | | |
|---|---|---|---|
| 2002/0183959 | A1 | 12/2002 | Savill et al. |
| 2007/0074359 | A1* | 4/2007 | O'Lynn ............... A46B 15/0002 15/105 |
| 2007/0265495 | A1 | 11/2007 | Vayser |
| 2007/0270221 | A1* | 11/2007 | Park .................. A46B 15/0002 463/37 |
| 2009/0215015 | A1 | 8/2009 | Chu |
| 2009/0291422 | A1* | 11/2009 | Puurunen ........... A46B 15/0006 434/263 |
| 2009/0317770 | A1* | 12/2009 | Gatzemeyer ....... A46B 15/0002 433/215 |
| 2010/0319145 | A1* | 12/2010 | Neyer .................. A61C 17/221 15/22.1 |
| 2010/0323337 | A1* | 12/2010 | Ikkink ................ A46B 15/0002 434/263 |
| 2011/0010876 | A1* | 1/2011 | Iwahori .............. A46B 15/0002 15/22.1 |
| 2011/0275424 | A1* | 11/2011 | Schmid .............. A46B 15/0002 463/1 |
| 2011/0313825 | A1 | 12/2011 | Wilhelm et al. |
| 2012/0036657 | A1* | 2/2012 | Iwahori .............. A46B 15/0006 15/22.1 |
| 2012/0246858 | A1* | 10/2012 | De Vries ............ A46B 15/0002 15/167.1 |
| 2012/0251975 | A1* | 10/2012 | Iwahori .............. A61C 17/3481 433/119 |
| 2012/0266397 | A1* | 10/2012 | Iwahori .............. A46B 15/0006 15/22.1 |
| 2013/0125326 | A1* | 5/2013 | Schmid .................... A46B 9/04 15/105 |
| 2013/0125327 | A1* | 5/2013 | Schmid .................... A46B 9/04 15/105 |
| 2013/0132388 | A1* | 5/2013 | Patel ................. G06F 17/30386 707/736 |
| 2013/0137074 | A1* | 5/2013 | Meriheinae ........ A46B 15/0006 434/263 |
| 2014/0033034 | A1* | 1/2014 | Patel .................. A46B 15/0006 715/716 |
| 2014/0065588 | A1 | 3/2014 | Jacobson et al. |
| 2014/0165311 | A1* | 6/2014 | Donegan ............ A46B 15/0006 15/22.1 |
| 2015/0044629 | A1 | 2/2015 | Wang et al. |
| 2015/0374454 | A1* | 12/2015 | Beerstecher ........... A61C 17/04 433/27 |

FOREIGN PATENT DOCUMENTS

| | | | |
|---|---|---|---|
| EP | 3010411 A1 | | 4/2016 |
| JP | 2009-240760 | * | 10/2009 |
| WO | WO 2002/083257 | | 10/2002 |
| WO | 2006/137648 | * | 12/2006 |
| WO | 2010/134050 | * | 11/2010 |
| WO | WO 2012/020165 A1 | | 2/2012 |
| WO | 2012/034786 | * | 3/2012 |
| WO | 2014202250 A1 | | 12/2014 |
| WO | 2014202438 A1 | | 12/2014 |
| WO | 2016180929 A1 | | 11/2016 |

OTHER PUBLICATIONS

International Search Report and Written Opinion for PCT/EP2016/060715 dated Jul. 26, 2016, 8 pages.
International Search Report and Written Opinion for PCT/EP2016/055407 dated Nov. 25, 2016, 13 pages.
Chang et al., Playful Toothbrush: UbiComp Technology for Teaching Tooth Brushing to Kindergarten Children; CHI 2008, Apr. 5-10, 2008; 10 pages; Florence, Italy.
Barras, Computerised toothbrush makes oral hygiene a game; New Scientist; https://www.newscientist.com/article/dn13598-computerised-toothbrush-makes-oral-hygiene-a-game/; Apr. 2008; 3 pages; 26th Computer and Human Interaction conference in Florence, Italy.
PCT/EP2014/056844 International Application No., International Search Report dated Aug. 1, 2014.
PCT/EP2014/056844 International Application No., Written Opinion dated Jun. 5, 2015.
Schechner, Sam, "These Gadgets Aim to Put Some Teeth Into the Internet of Things," The Wall Street Journal, vol. CCLXIII, No. 50, Mar. 3, 2014 (2 pages).
Third-Party Observations Under Article 115 EPC in European Patent Application No. 14716781.1, dated Mar. 23, 2018 (5 ppages.
Third-Party Observations Under Article 115 EPC in European Patent Application No. 14716781.1, dated Apr. 11, 2018 (18 pages).
Third-Party Observations Under Article 115 EPC in European Patent Application No. 14716781.1, dated Apr. 24, 2018 (36 pages).
Article 94(3) Communication from the Examining Division in European Patent Application No. 14716781.1, dated May 2, 2018 (6 pages).

* cited by examiner

TOOTHBRUSH SYSTEM WITH SENSORS FOR A DENTAL HYGIENE MONITORING SYSTEM

CROSS REFERENCE TO RELATED PATENT APPLICATION

The present application is a National Stage Application of International Application No. PCT/EP2014/056844 entitled "TOOTHBRUSH SYSTEM WITH SENSORS FOR A DENTAL HYGIENE MONITORING SYSTEM" filed Apr. 4, 2014, which claims priority to U.S. Provisional Application No. 61/836,837 filed Jun. 19, 2013, the contents of which are incorporated herein by reference in their entirety.

FIELD

The present invention relates to methods and devices for monitoring tooth brushing activities.

BACKGROUND

According to the CDC, although preventable, tooth decay is the most common chronic disease of children aged 6-11 (25%) and adolescents aged 12 to 19 years (59%). Also 28% of adults aged 35 to 44 have untreated tooth decay. A bacterial biofilm called plaque that develops on teeth contributes to tooth decay and gingivitis. However, plaque can be removed by brushing at least once a day for two minutes and preferably twice a day and therefore prevent or mitigate tooth decay. Atlin T and Horecker E., "Tooth Brushing and Oral Health: How Frequently and When Should Tooth Brushing be Performed" Oral Health & Prevention Dentistry, 2005 3 (3): 135-140. Additionally, research shows that children continually miss the same areas during brushing which leads to isolated buildups of plaque on certain teeth. Accordingly, more important than the length of time of brushing, is the efficacy of the tooth brushing. Additionally, dental health education only has been shown to generally only have a small and temporal effect on plaque accumulation. Atlin T and Horecker E., "Tooth Brushing and Oral Health: How Frequently and When Should Tooth Brushing be Performed" Oral Health & Prevention Dentistry, 2005 3 (3): 135-140. Furthermore, many toothpastes incorporate fluoride with promotes the regrowth of tooth enamel to prevent cavity formation. According to the American Dental Association, the compliance with tooth brushing is quite low. For instance, only 49% of men and 57% of women brush their teeth twice a day.

SUMMARY

Accordingly, there exists a need for a dental system that could increase a user's compliance of tooth brushing with dentist recommend regimes in order to decrease cavities, gum disease, and other dental complications from lack of brushing. The present disclosure provides systems and methods for monitoring toothbrush usage and electronically providing feedback and other incentives to the user to increase compliance.

The system allows the recording of teeth brushing activities and the analysis of those activities. It allows the creation of a service that provides feedback and incentives for a user of the tooth brush system. The toothbrush records brushing data through sensors during its use. In some embodiments, the data is analyzed and compared to reference data. Through a feedback output device, the user receives advice about the use of the system and incentives and other feedback designed to increase compliance with recommended usage regimes. For example, the system may implement a gamification process to increase the motivation to use the hygienic device.

In some embodiments, the invention relates to a method for a new way to use a toothbrush by informing a user about his/her brushing practices for example by wireless integration with a mobile telecommunication device having a display screen apart. The electric tooth brush may also communicate data wirelessly to a base station which may then send the data to a network for analysis on cloud servers or wirelessly to a mobile device. The mobile telecommunication device may be a mobile phone, a microcomputer with telecommunication means, a tablet computer with telecommunication means. In other embodiments, the data may be wirelessly sent to the base station and then uploaded to servers for later accessing by computing devices that include both mobile and non-mobile computing devices.

The toothbrush system may include a toothbrush with sensors and a base station, the base station physically supporting the toothbrush when it is not handled by a user. The electronic toothbrush may include (a) signal processing circuitry, (b) memory, (c) base station interface for exchanging data between the toothbrush and base station, (d) a power supply circuit that may include a rechargeable battery or capacitor, and (e) a controller. The base station may include (a) a network interface for exchanging data between the internet or other network and the base station, and (b) a recharging circuit for recharging the toothbrush's rechargeable battery. In other embodiments, the system may not include a base station and signals may be sent wirelessly directly to a mobile phone or other wireless terminal.

Electrical Configuration

The controller of the toothbrush may be configured to coordinate the data exchange between the toothbrush and the base station and/or mobile device for the transfer of the processed signals from the sensors to the base station. In some embodiments, the toothbrush system 100 may include signal conditioning circuits for the processing of signals from the sensors, a memory for the storing of the processed signals from the sensors, a toothbrush interfacing circuit for allowing information exchanges between the toothbrush and the base station, a toothbrush power supply circuit for powering the sensors and the circuits of the toothbrush, including a rechargeable electric source of the battery and/or capacitor type, and a controller circuit for directing the operation of the tooth brush electronics.

The base station may include the following circuits: a data exchange circuit for exchanging data with a network, a base station interfacing circuit adapted to exchange information with the toothbrush, a base station power supply circuit for powering the base station circuits and for recharging the rechargeable electric source of the toothbrush when it is received in the base station. The controlling circuit may be configured to store in memory the processed signals from the sensors upon the detection of the user using the toothbrush, and to command, when the toothbrush is received in the base station, the data exchange circuit of the base station to transfer the stored signals from the sensors, through the interfacing circuits of the toothbrush and of the base station, over the network.

Physical Design

In some embodiments, the toothbrush may include an electronic motor, for vibrating the toothbrush head during brushing. Additionally, the head of the toothbrush that includes the bristles, may be removably connectable to a body or handle of the toothbrush, and be configured for the interchangeability of multiple heads. The toothbrush may be waterproof. In some embodiments, a base station may be configured to physically receive only one, two, three, four or five, or additional numbers of toothbrushes.

Sensors

The sensors of the toothbrush may be one or more of: i) a pressure sensor (10) motion sensors (11), or ii) any other type(s) of sensors capable of measuring brushing activities of the toothbrush, such as an accelerometer or an inertial sensor. This may include accelerometers, magnetometers and gyroscopes. In some embodiments, the toothbrush may include at least a pressure sensor and at least one acceleration sensor. In some embodiments, the processed signals from the sensors are transferred to the server via a network through the base station. Additionally, processed signals from the sensors are transferred to the server via a network through the mobile device.

Computing Devices

In some embodiments the mobile telecommunication device is a mobile phone, a microcomputer with telecommunication means, a tablet computer with telecommunication means, or any other means having display means for displaying information related to a tooth brushing activity and having circuits for a connection to the global network and for communicating with the global network. For example, the mobile device can typically be a mobile phone, but may also consist of other portable mobile PDA device types ("PDA") or otherwise, with capacity of radio communication or, even, a microcomputer laptop or desktop with telecommunication means, a tablet computer with telecommunication means. In other embodiments, the signals are viewable on a stationary computable device that accesses the data via cloud servers.

Signal Processing

The controller of the toothbrush is configured to store processed signals from the sensors in memory. The controller coordinates the acquisition, processing, and storage of signals once the controller or other processor in the system determines a user initiates brushing. Next the controller may be configured to send the stored signals wirelessly to the base station or the computing device for further processing, display, or analysis.

Signal processing may include filtering, amplification, conversion, signal conversion from analog to digital, digital filtering, digital data compression, digital data reduction, digital data computation, and digital data conversion.

Data Protocols and Transfer

In some embodiments, the toothbrush interface circuit and the base station interface circuit are wireless circuits, for example: WiFi®, Bluetooth®, GSM/UMTS and derivatives. In some embodiments, the data exchange circuit of the base station uses a wireless protocol, for example: WiFi®, Bluetooth®, GSM or others. In some embodiments, the toothbrush may have a unique identifier, to allow the pairing of a mobile device and the toothbrush.

In other embodiments, the toothbrush interface circuit and the base station interface circuit may utilize wired connections. For example, the data exchange circuit connection to the network is wired. Identification data may be incorporated in the data packets that include the stored signals from the sensors that are sent over the network. The identification may include a serial identity number of the toothbrush or head, a serial identity number of the base station, or a network address of the base station. Additionally, tooth brushing monitoring data obtained during the measuring step may be time-stamped using data from a toothbrush internal clock.

In other embodiments, the network comprises at least a wireless local area network (WLAN) and during the step of communication, the toothbrush transmits data to said mobile device via said WLAN. The WLAN may operate according to a communication protocol selected from the Wifi or Bluetooth protocols. A mobile or other computing device may also be in communication with the local wireless local area network and in the communication step, the tooth brush transmits said data to the mobile device via said wireless LAN.

The LAN may include a server that communicates with at least the toothbrush, and in the communication step, the toothbrush may transmit said data to the mobile device by means of the server. The telecommunication network may further comprise a network of separate remote wireless LANs, the server communicating with at least one server via said remote network, the mobile device also communicating with said server via the remote network.

The information exchanged between the toothbrush and the base station through the interfacing circuits may include data or commands, the data including stored, processed signals from the sensors. Information may be transmitted from the toothbrush to the base station and, conversely, from the base station to the toothbrush, as needed. The data can also be a program or software update to store and/or execute by the toothbrush. For example, updates and new firmware may be wirelessly downloaded and installed on the toothbrush.

Cloud Server or Local Network Processing of Data

In some embodiments, the system includes a server and the stored, processed signals from the sensors are transferred over the network to said server, the server including storing means for the transferred processed signals and including computational components under the control of a program or software instructions. The program has instructions that are configured to send, at the end of the transfer, an erase command over the network to the toothbrush to erase the signals stored on the toothbrush that have been transferred to the server. The server may also determine the location of the tooth brush using geolocation capabilities of the remote network and/or of the mobile device.

The server includes memory for storing a history of the successive transferred stored and processed signals from the toothbrush sensors. The program for controlling the computational components of the server includes software instructions for analyzing and comparing the stored and processed signals and to provide computational results from said analysis and comparison. The program for controlling the computational components of the server may include instructions for making the results of the analysis available to a variety of computing devices, including a mobile or stationary device, by accessing the server through an internet page or other variety of methods. The computational analysis from the server may be transferred or downloaded directly to a computing device via a network link 35, which may be made through a dedicated communication equipment POA link 34 to the base station. Accordingly, the computational results from the server are transferred to the mobile device via a network through a dedicated communication equipment POA, and then to the base station and/or the toothbrush via links 33, 31, and 32. When the tooth brush is operative and communicating with the server, said server can update the software and/or the parameters running and/or used in the toothbrush. Similarly, the server can update the application or parameters related to the toothbrush and which is running on the mobile device.

User Profile

The system may include a stored user profile associated to the tooth brushing activity and its related data comprises the age, size and gender of the user. During or after the step of monitoring tooth brushing activities, the toothbrush, mobile device, or server automatically seeks to match the user with at least one user profile using at least one predetermined rule depending on the user profile and of past data. If the user is not a regular user of the toothbrush, said user identifies him/her as a guest on the mobile device.

In a step of user identification, a specific user may be associated with the toothbrush and presumed to be the user. If multiple users for a given toothbrush are utilized, to associate a user with a brushing activity at least in the toothbrush and possibly in the mobile device and/or the server at least for reference purposes for those last two.

Data Output

In some embodiments, the toothbrush transmits data in real time to the mobile or other computing device, and in the display step, the computing device displays in real time on the screen, information related to said data, for example the instantaneous progress of a user for a brushing episode in progress.

Calibration/Initialization

In some embodiments, the toothbrush may be calibrated, either in the factory or by the user. If the calibration step is performed by the user, said user can be guided in this process by information given by e.g. the display of the mobile device.

In a step of initialization, the system may allow for the selection of the desired local wireless network or mobile device. This can be done automatically or with the help of the user, and these operations correspond to a network pairing between the elements of the system which communicate between them. In some embodiments, the toothbrush may include at least a pressure sensor, at least one acceleration sensor, signal conditioning circuits for the processing of signals from the sensors, a memory circuit for the storing of the processed signals from the sensors, a toothbrush interfacing circuit for allowing information transfer between the toothbrush and a base station, a toothbrush power supply circuit for powering the sensors and the circuits of the toothbrush, said toothbrush power supply including a rechargeable electric source of the battery and/or capacitor type, and a controlling circuit for the operation of the toothbrush circuits. Preferably, the controlling circuit is configured to store in the memory the processed signals from the sensors upon the detection of the user using the toothbrush, and to command, when the toothbrush is received in a base station, the data exchange circuit of the base station for the transfer of the stored, processed signals from the sensors, through the interfacing circuits of the toothbrush and of the base station, over a network.

According to the invention, the base station includes a data exchange circuit with a network, a base station interfacing circuit adapted to exchange information with a toothbrush according to the invention, a base station power supply circuit for powering the base station circuits and for recharging the rechargeable electric source of the toothbrush when it is received in the base station.

From another point of view of this same invention, the invention provides a system and also a method using the system for monitoring tooth brushing activities, allowing communications with a mobile communication device having a display and information entry means, the toothbrush and the mobile device communicating both by radio with a telecommunications network, said telecommunications network being adapted to make communicate at least the mobile device with at least one further telecommunications device, the method comprising the steps of: (a) at least one tooth brushing activity monitoring step in which the toothbrush performs at least one measurement indicative of at least the brushing activity of the user, (b) at least one stage of two-way communication during which: i) a user enters information in the mobile device, and the mobile device transmits said information to the toothbrush through the telecommunication network, and ii) the toothbrush transmits to the mobile device, the data according to said tooth brushing activity monitoring measurement, through the telecommunications network, and (c) at least a display or feedback step in which the mobile device displays on its screen information based on tooth brushing activity monitoring data transmitted in the communication step. The displayed information may be representative of an output of a computation done on the transmitted data, said computation being done in the mobile device or in a server.

The present discloses provides a product and service which improves the use and/or motivation for a user to brush their teeth. Feedback is provided through an output device linked with the system. The system provides a toothbrush including sensors which monitor a user's brushing activities and provides feedback related to the brushing to the user. In some embodiments, a server may provide applications that use and process the data received from the sensors to provide output data relating to the quality of the brushing and other analysis. Finally, the applications running on the server may process this output data to provide feedback to the user to provide a playful/gameful dimension to increase the motivation to brush the user's teeth.

BRIEF DESCRIPTION OF THE DRAWINGS

The invention will now be described in relation to an exemplified embodiment and to the following Figures.

DETAILED DESCRIPTION

Figure 1:
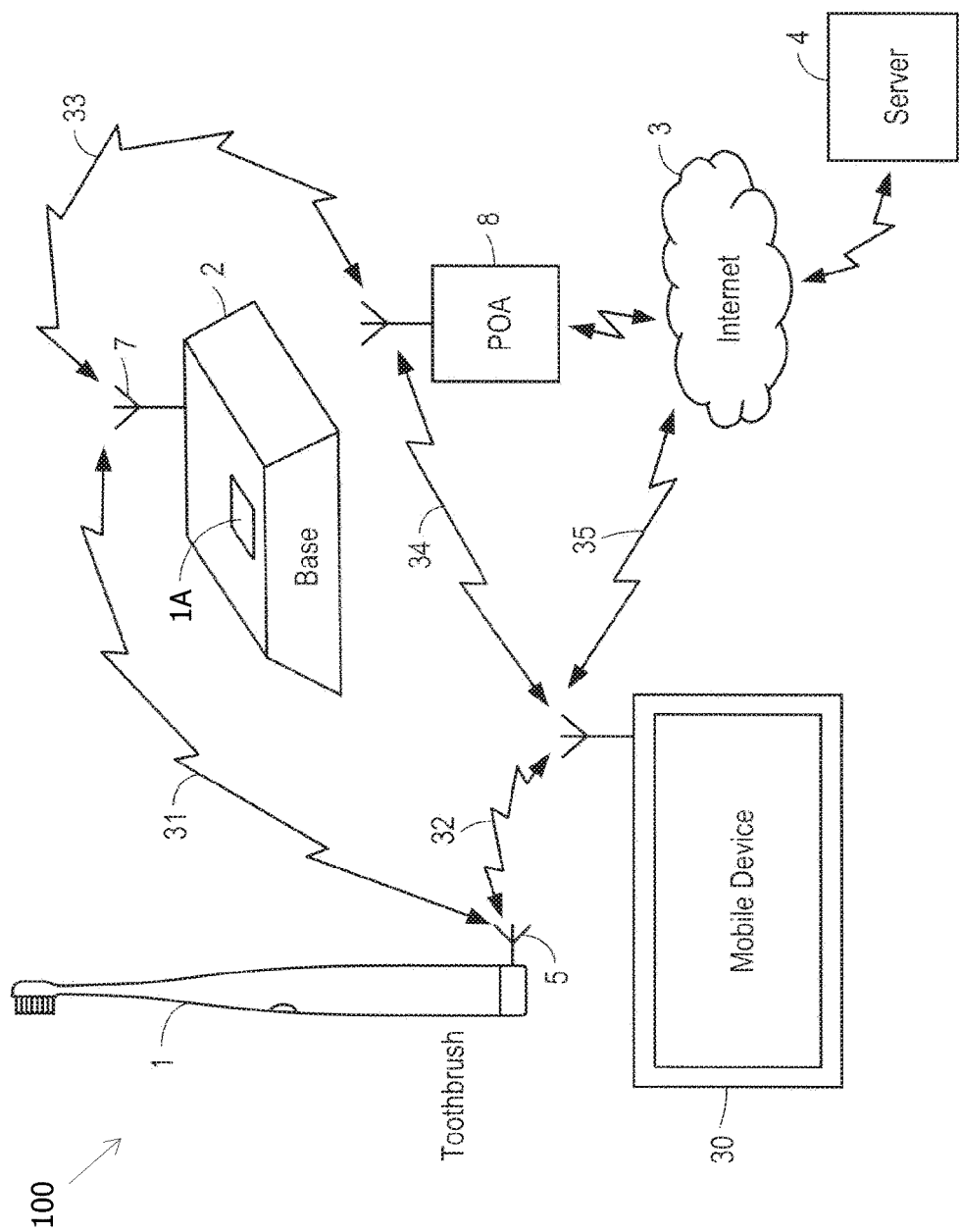
FIG. 1 which is a schematic view of the system of the invention.

Various examples of the invention will now be described. The following description provides specific details for a thorough understanding and enabling description of these examples. One skilled in the relevant art will understand, however, that the invention may be practiced without many of these details. Likewise, one skilled in the relevant art will also understand that the invention can include many other obvious features not described in detail herein. Additionally, some well-known structures or functions may not be shown or described in detail below, so as to avoid unnecessarily obscuring the relevant description.

The terminology used below is to be interpreted in its broadest reasonable manner, even though it is being used in conjunction with a detailed description of certain specific examples of the invention. Indeed, certain terms may even be emphasized below; however, any terminology intended to be interpreted in any restricted manner will be overtly and specifically defined as such in this Detailed Description section.

Particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly while operations may be depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

FIG. 1 illustrates an overview of the disclosed toothbrush monitoring and feedback system 100 that includes: a toothbrush 1 equipped with sensors, a base station 2 for receiving and charging the toothbrush 1, a mobile device 30 that wirelessly receives/sends data, a dedicated wireless link POA 8, a server 4 and a network 3 for transferring the information from the server or between other various components of the system 100.

Data Communication

The toothbrush 1 has an antenna 5 and transceiver means for radio communication to a compatible complementary antenna 7 and transceiver means of the base station 2 through a radio link 31. The radio-communication link 31 may be for example WiFi or GSM or Bluetooth or their derivatives or other proprietary protocols.

In another embodiment, antennas and transceiver means are replaced or completed by wired connections or connectors to allow the exchange of information between the toothbrush 1 and the base station 2. Wired connectors may also provide electric power supply from the base station to the tooth brush for recharging a rechargeable electric source of the latter. In another embodiment, the electric power supply from the base station to the tooth brush is provided with electromagnetic induction circuitry.

The base station 2 may be powered through a power cord. The base station 2 may alternatively be powered by a rechargeable battery which is charged from time to time with a battery charger powered by the power supply grid. The base station 2 has a receiving slot 1A for physically supporting and storing the tooth brush when it is not used by a user.

The base station 2 includes a data exchange circuit, for communicating data with a network 3, for example the internet. Data may be transferred using a radio-communication link 31, as illustrated in FIG. 1, with the antenna 5 of the base station 2 and with the antenna of a dedicated communication equipment 8 or POA, connected to the network 3. In other embodiments, transfer of data between the base station 2 and the network 3 are performed through a wired link, for example ADSL.

The antenna 5 and transceiver means of the toothbrush 1 is also compatible with radio communication means of a mobile device 30 over a radio link 31. The radio-communication link 31 is for example WiFi or GSM or Bluetooth or their derivatives or other suitable protocols. In some embodiments, radio links 31 are short range, local, radio communication links or a radio link 35 such as the ones used in cellular or other mobile phone systems (GSM and derivatives for example).

The mobile device 30 is also able, via its radio communication circuits, to exchange data on a radio link 31 through the dedicated communication equipment 8 or POA, on the network 3. In addition or alternatively, the mobile device 30 is able to exchange data on a radio link 35 directly on the network 3.

A server 4 is connected to the network 3 by any suitable means. Server 4 is defined broadly to include computing devices capable of storing and computational operations for example on the "cloud" in a computing network. The server 4 may include storage devices, for instance memory, hard disk drives, flash memory, or other storage devices and includes computational means under the control of a program. For the transfer of data, the toothbrush controlling circuit uses a predetermined server 4 address of the network 3. This predetermined address may be stored initially in the toothbrush 1 and/or updated later through the network 3. The transfer of data between the toothbrush 1 and server 4 may be performed: a) each time the toothbrush 1 is replaced in the base station 2 in a batch configuration, b) at the direction of the user or the server 4, for example by user action initing the transfer using the interface of the mobile device 30 or a web page accessing the server 4 or c) in real time when toothbrush 1 activities are detected, or d) the toothbrush 1 is removed from the base station 2 or e) at other suitable intervals.

System Circuit Design and Network Architecture

Figure 2:
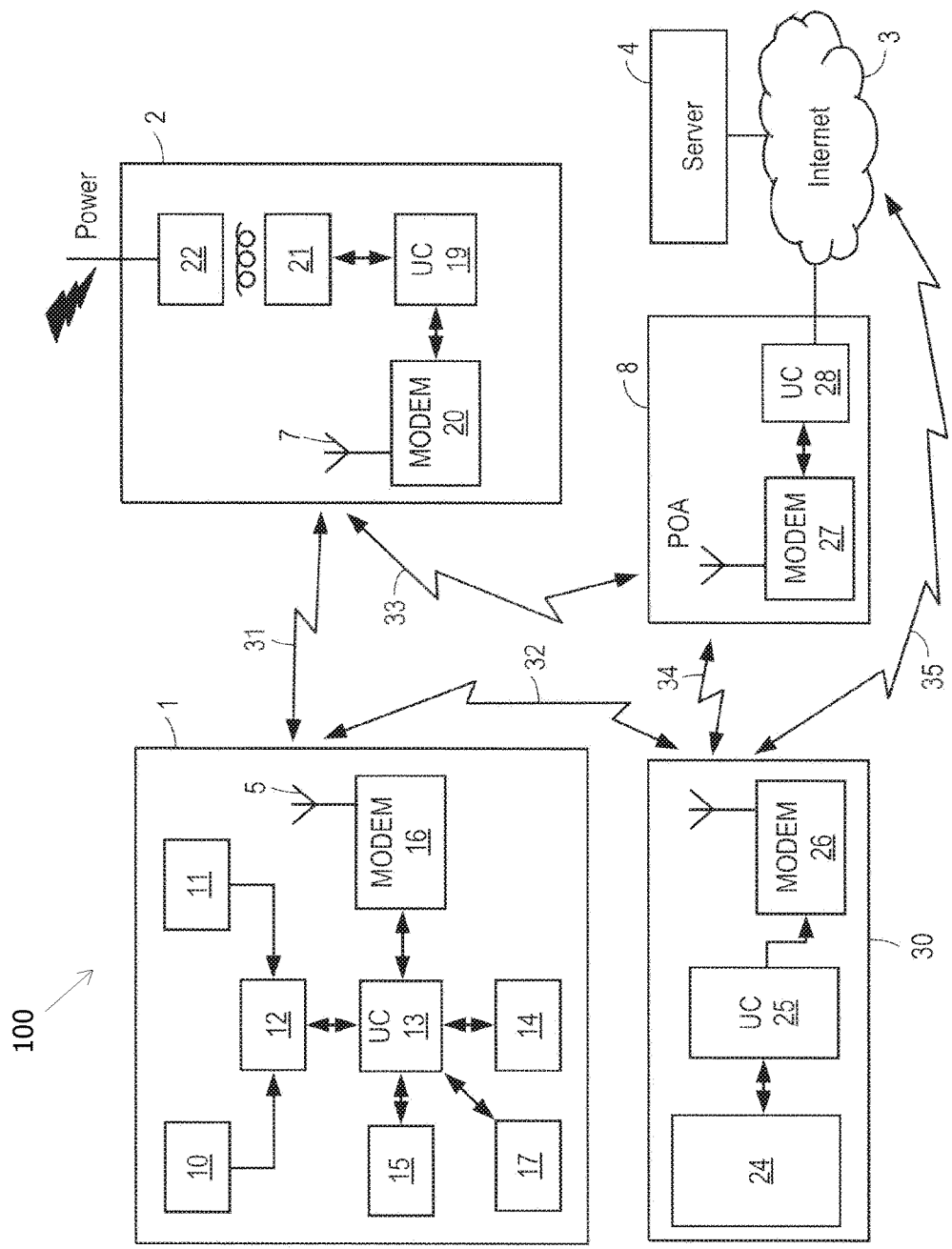
FIG. 2 is a diagrammatic view of the toothbrush and of the base station of the system.

As illustrated in FIG. 2, the toothbrush 1 may include a pressure sensor 10 and at least one motion sensor 11. The pressure sensor 10 detects force applied on the brushing side of the toothbrush 1 when a user applies the bristles to their teeth. A motion sensor 11 may be provided for detecting motion on any or all three of the orthogonal axes of the toothbrush 1, or a motion sensor may be able to detect accelerations or other motion characteristics in all three axes. The signals output by the sensors are processed by a signal conditioning circuits 12. Examples of signal conditioning include: frequency and noise filtering, amplification, conversion, digital signal processing, and other techniques to optimize the detected signals for analysis.

The processed signals from the sensors are then stored in memory 14 as determined by a controller 13 which may be a digital signal processor, microcontroller, or other processing component and which operations are controlled by a program 15. The memory 14 may be included in the toothbrush 1 or on a server 4 or other component of the system 100. A program 15 may be updated through a toothbrush 1 interfacing circuit 16, a modem for radio communication, and its antenna 5 (and/or connector in case of contact/wired interface) or other interfaces of the toothbrush 1. More generally, the toothbrush interfacing circuit 16 allows information exchanges between the toothbrush 1 and the base station 2 when the radio link 31 is established (and/or connectors of the tooth brush and of the base station are mated together). The toothbrush 1 may contain a power supply circuit for powering the sensors and the circuits of the toothbrush 1 and it can include a rechargeable electric source 17.

The base station 2 may include a base station interfacing circuit 20, a modem for radio communication, with an antenna 7 (and/or connector) to exchange information over link 31. In addition, the base station interfacing circuit 20 is able to establish a radio link 33 with the dedicated communication equipment 8, for communication with the network 3. The base station 2 may utilized a power supply converter 22 which is regulated 21 to provide appropriate voltage and current to the base station circuits. Electrical connections (not illustrated) for providing charging current to the toothbrush 1 from the base station 2 may be provided.

In some embodiments, the base station 2 is passive and its circuits are under the control of the controller 13 of the tooth brush 1 when they are communicating together, specifically when the link 31 is of the wired/contact type with connectors. In the embodiment represented on FIG. 2, the base station has a controller 19 which controls its operations.

The dedicated communication equipment 8 may include a radio modem circuit 27 and the appropriate electronics for communicating with network 3. The dedicated communication equipment 8, is able to establish a radio link 31 with the base station 2 and/or a radio link 31 with the mobile device.

The mobile device 30 includes at least a radio modem 26 for establishing a radio link 31. The operations of the mobile device 30 are under the control of a controller 25, namely a central processing unit or μC, and of a program 15. The mobile device 30 includes an output means such as a display screen and an input means such as a virtual or material keyboard. Preferably, the input and output means of the mobile device 30 are used in the system to input information and to display information, notably the results of computations performed by a server.

The program of the computational means of the server 4 allows storage of signals received from the toothbrush 1. Additionally the server 4 may analyze the data from the sensors to produce feedback and motivational data regarding the user's performance in brushing their teeth. These results may be accessible to the user on an internet page hosted by the server 4 or transferred to another webserver for hosting. In a different embodiment, the previous operations and computations are done fully or partially in the mobile device 30, the server 4 being used for general monitoring.

It should initially be understood that the disclosure herein may be implemented with any type of hardware and/or software, and may be a pre-programmed general purpose computing device. For example, the system may be implemented using a server, a personal computer, a portable computer, a thin client, or any suitable device or devices. The disclosure and/or components thereof may be a single device at a single location, or multiple devices at a single, or multiple, locations that are connected together using any appropriate communication protocols over any communication medium such as electric cable, fiber optic cable, or in a wireless manner.

It should also be noted that the disclosure is illustrated and discussed herein as having a plurality of modules which perform particular functions. It should be understood that these modules are merely schematically illustrated based on their function for clarity purposes only, and do not necessary represent specific hardware or software. In this regard, these modules may be hardware and/or software implemented to substantially perform the particular functions discussed. Moreover, the modules may be combined together within the disclosure, or divided into additional modules based on the particular function desired. Thus, the disclosure should not be construed to limit the present invention, but merely be understood to illustrate one example implementation thereof.

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Implementations of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer to-peer networks).

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The operations described in this specification can be implemented as operations performed by a "data processing apparatus" on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a standalone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

Toothbrush Design

Figure 3A:
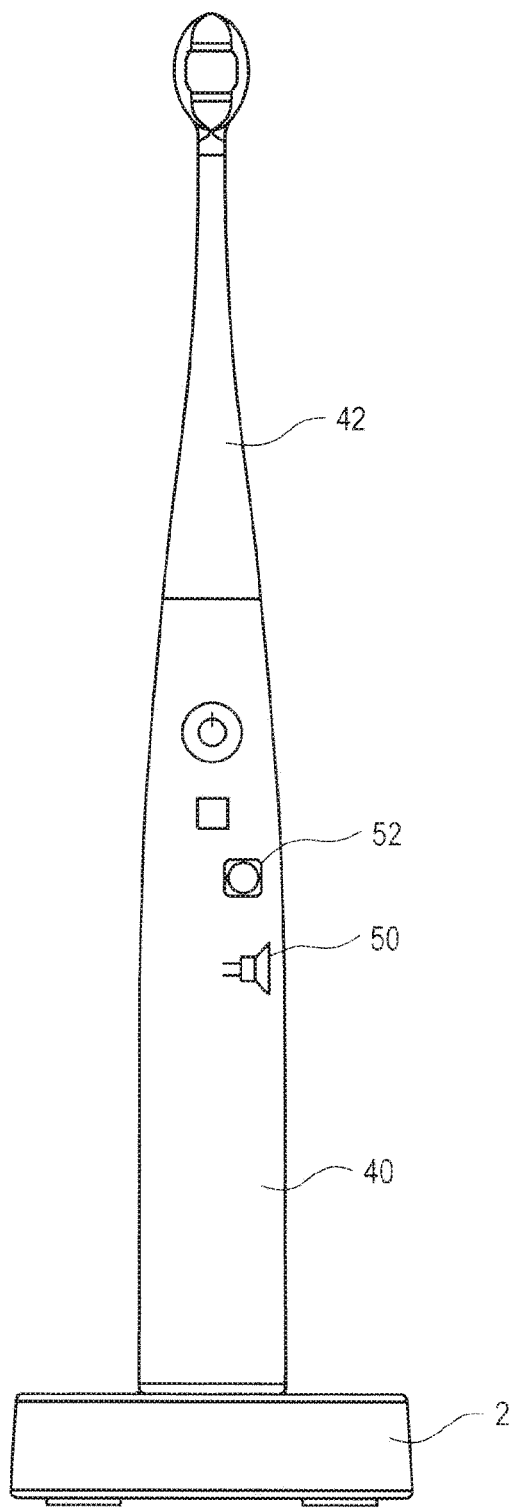
FIG. 3A is a perspective view of a toothbrush and head in accordance with one embodiment of the present invention.
Figure 3B:
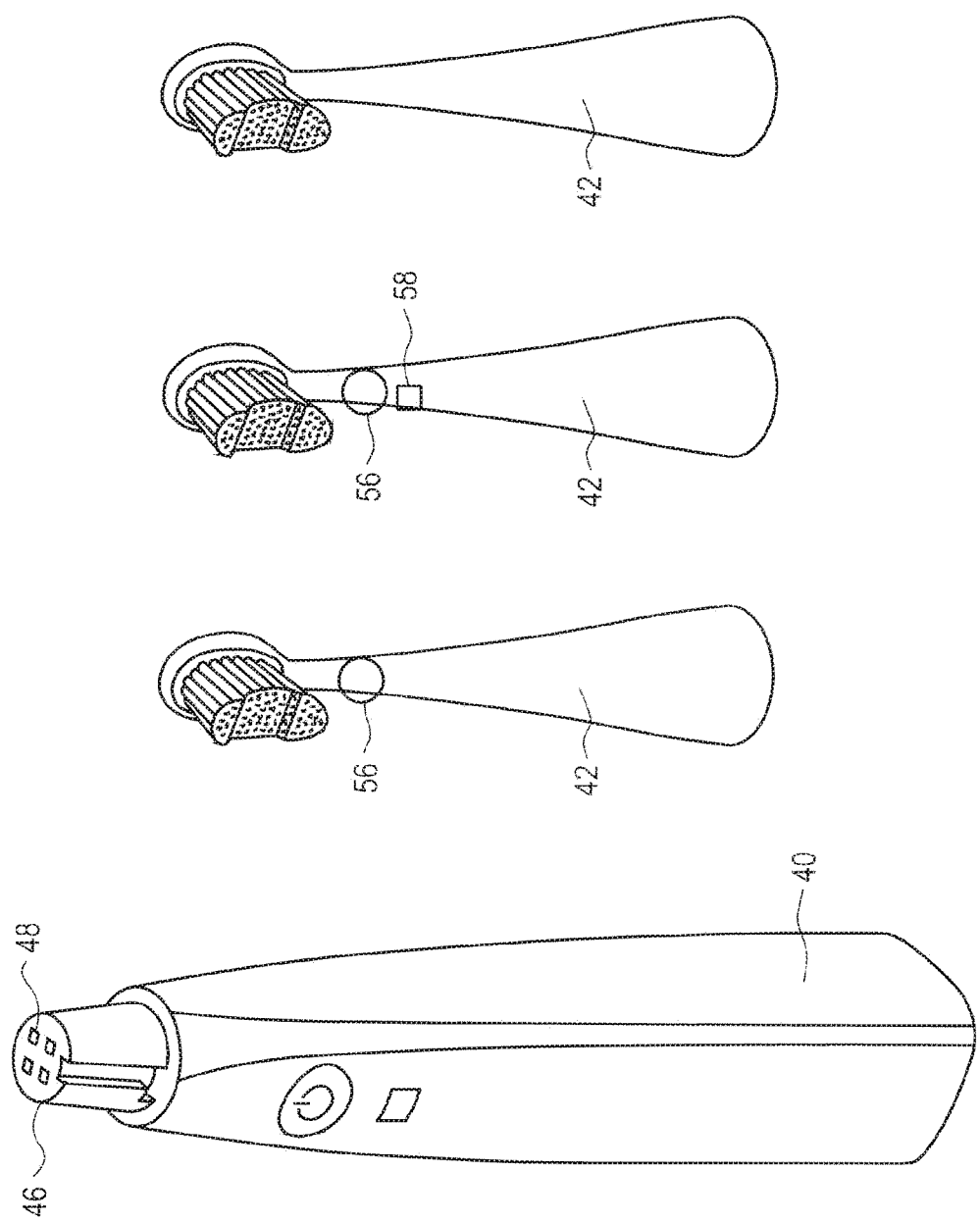
FIG. 3B is a perspective view of a toothbrush handle and replaceable heads that may be attached to a head interface.

As illustrated in FIG. 3, the toothbrush 1 includes a handle 40, and a head 42 that may be removably connectable to the handle 40. The handle 40 may contain a motor that is mechanically connected to the head 42 and when activated vibrates or moves the head 42 in manner that brushes a user's teeth when placed inside the mouth. The handle 40 includes a head interface 46 that removably attaches various heads 42 to the handle 40. The head interface 40 contains leads 48 for both data and power transfer to various heads 42. For example, certain heads 42 may include sensors that require power and data transfer, and therefore power can be routed from the handle's 40 power source to the head 42 through leads 48 that form a connection with the head 42 at the head interface 46. The may be various numbers of leads 48 that form the connection on the head interface 46, for instance there may be two leads 48 for power, and two leads 48 for data, three leads 48 for power, three leads 48 for data, and other various numbers of leads. In some embodiments the head interface 46 will form a watertight seal with the head 42 to prevent water from entering the interface and interfering with the electrical leads 48 power and data transfer.

In some embodiments, the majority of the circuitry and costly components can be contained inside the handle 40 as opposed to the head 42, which may be disposable after a certain number of uses. This will minimize the cost of the replacement heads 42. For example, in some embodiments, the battery, controller 13 may be contained in the handle 40, and any sensor probes and circuitry to connect the sensor probes may be contained in the head 42. In other embodiments, the head 42 may contain no circuitry or electrical components and will only provide a mechanical brushing function by supporting the bristles.

The toothbrush 1 may also include a speaker 50 and various visual indicators 52 to provide audio and visual feedback to the user. For example, the handle 40 may contain a speaker 50 for playing music, substantive feedback, motivational phrases, remaining time elapsed, recommendations on brushing pressure, on whether certain quadrants have not been adequately brushed, an announcement for completion of brushing, etc. Additionally, the toothbrush 1 may contain any number of visual indicators 52, for providing substantive feedback on the brushing including time elapsed, a LED indicator for when brushing is complete, warning indicators for brushing inappropriately, including indicators for whether each quadrant has been addressed. In other embodiments, the toothbrush 1 may also utilize osteophony to convey audio messages to the user.

Sensors

The toothbrush 1 may incorporate various sensors that detect certain attributes of brushing that may be analyzed to provide various feedback and other motivational information to the user. For example, the toothbrush 1 may incorporate various motion sensors 11 to determine the quality of the brushing with respect to certain quadrants of the mouth or even individual teeth. The motion sensors 11 may include gyroscopes, accelerometers, magnetometers, and other various sensors capable of detecting positions, movement, and acceleration. These various motion sensors 11 may be incorporated either in the handle 40 or the head 42. However, it may be advantageous to put the motion sensor 11 in the handle 40 in embodiments where the head 42 and therefore any acceleration or other motion sensor would experience at lot of additional motion that may interface with detecting a position.

The toothbrush 1 may also incorporate various proximity sensors that detect the proximity of the toothbrush 1 to the mouth of a user. These may be incorporated at the head 42 or in the handle 40. The proximity sensors may be utilized to acquire additional positional information relevant to determining the brushing quality of the user.

Additionally, the toothbrush 1 may contain a pressure sensor 10 to determine whether the user is applying appropriate pressure in brushing their teeth. The pressure sensor 10 may be incorporated into the head 42 which may be more easily flexible or utilize simple pressure transducers or other components capable of measuring pressure.

In some embodiments, various heads 42 may incorporate a camera 56 that will detect various aspects of tooth quality that may or may not be related to brushing quality. For example, a camera 56 including a near infrared camera 56 may be able to be utilized on a toothbrush 1 to collect data indicative of demineralization or dental caries or dental decay. For example, the toothbrush 1 may utilize certain wavelengths that are particularly suited to detect these abnormalities, for instance in the 1300-1400 nm range. In some embodiments, the toothbrush 1 may also contain a light source 58 that will be focused towards the teeth during brushing and can be utilized by the camera to detect certain abnormalities.

Certain cameras 56 and potentially light sources 58 may also be implemented to detect levels of plaque on the teeth and changes in levels of plaque during brushing. In certain embodiments, infrared or near-infrared light sources 58 and an appropriate camera 56 that detects and records light in this wavelength range may potentially allow for the detection of plaques.

Program for Brushing Analysis and Feedback

The toothbrush's 1 various sensors may gather data relevant to the quality of brushing by a user or the overall dental health of a user's teeth. This data may then be processed using programs or applications installed in various portions of the toothbrush monitoring system 100. Accordingly, as described above, data from the sensors may be processed by a program executed by the toothbrush's 1 controller 13 or alternatively a processor on the mobile device 30 or the server's 4. The system's 100 processing and analysis of the data will result in output data representing feedback relevant to a user's quality of brushing. This feedback may be communicated through audio feedback through the toothbrush 1 speaker 50, visually on the toothbrush 1 indicators 52, or both on an associated mobile device 30 or when accessed on a website hosted or in communication with the server 4.

Figure 4:
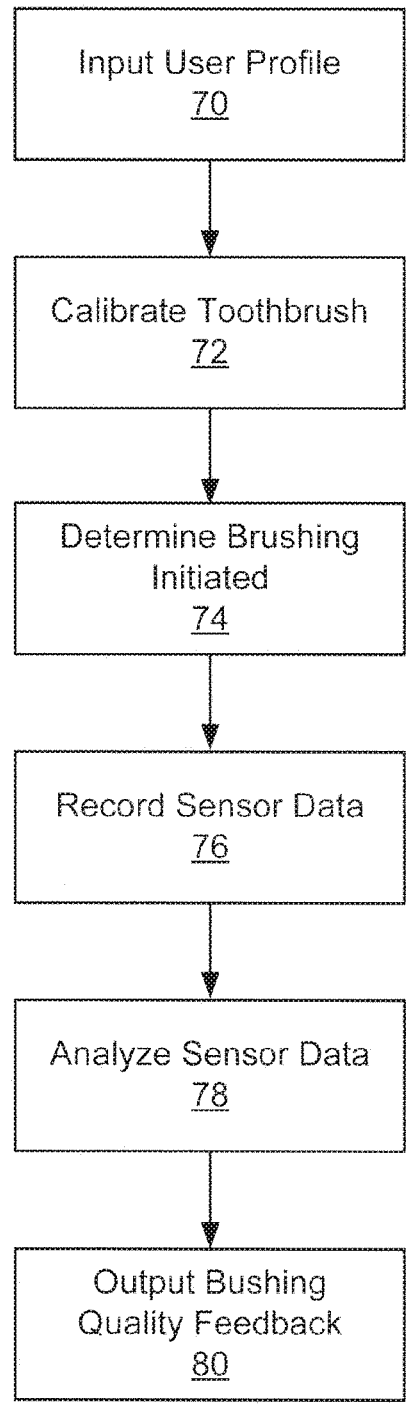
FIG. 4 is a flow chart illustrating an embodiment of a process utilized in the present disclosure to record brushing data and provide feedback to the user.

FIG. 4 illustrates an example of the process by which the toothbrush 1 evaluates the brushing quality of a specific user. Each the steps may not be required in a specific embodiment, but various combinations of these steps may be implemented in a toothbrush monitoring system 100. First, the user may input a user profile 70 into the toothbrush monitoring system 100, to allow the user to calibrate the toothbrush 72. After calibration, the user may pick up the toothbrush 1 and begin brushing her teeth. The toothbrush would then determine that brushing is initiated 74, and start recording sensor data 76 during brushing. Then the toothbrush monitoring system 100 may analyze the sensor data 78 to output brushing quality feedback 80 to the user.

User Profile

Accordingly, first a user profile may be entered 70 for each particular user of a certain toothbrush 1 or associated with a specific account stored on the server 4. Upon initialization for of a new toothbrush or new account on the server 4, a user may enter their information that may be utilized to determine optimal brushing times and characteristics. For example, a program 15 may first request a user's name, gender, height, weight, age, and certain questions on their dental history. The user profile may then be associated with certain data recorded during use of the toothbrush by the user, including calibration data that is specific to certain toothbrushes 1 or is generic and can be applied to any toothbrush 1 connected to the system 100.

Detecting Usage

A tooth brushing monitoring system 100 may also determine whether usage has taken place and the number of usages per day. In some embodiments, the toothbrush detects motion data through motion sensors 11 and analyzes the data to determine whether usage has occurred, or whether the brush has been moved or usage is feigned. When motion indicative of usage is detected, the toothbrush 1 may store the positional and motion data in its memory 14 for later analysis. For example, this will prevent the recording of false positives, for example when a user moves the brush in a medicine cabinet, or from children circumventing the system by briefly shaking the toothbrush.

For example, movement indicating usage may be associated with a certain acceleration level and/or frequency that is characteristic of a particular user. In other embodiments, a user may push a button or switch on the toothbrush 1 to wake up the sensors on the device, which will then begin recording data. Accordingly, the toothbrush 1 will determine when brushing is initiated 74. In some embodiments, this will be performed automatically, for example, upon the detection of certain accelerations and frequencies. Accordingly, once the user picks up the toothbrush, the motion sensors 11 may begin recording the data 76 and sending it to any of the various controllers 13 in the system 100 to analyze it 78 for characteristics associated with brushing. For instance, the toothbrush 1 will generally be resting on its base 2 pointing upwards prior to use, in an orientation that would not be suitable for brushing by a user holding the toothbrush 1. Accordingly, once the user picks up the toothbrush 1, the toothbrush 1 will generally be rotated roughly 45 degrees to be held primarily horizontal during brushing. Accordingly, one threshold criteria for determining that brushing is initiated 74 would be whether the toothbrush 1 has been titled within a certain angle range indicating the toothbrush 1 is horizontal or near horizontal. This could be an angle range of 20 degrees, 5 degrees, 10 degrees, or other suitable ranges. Additionally, a series of calibration sessions may indicate a suitable range.

In other embodiments, the determination of whether brushing has initiated 74 and whether or not it has ceased may be performed by the system 100 using a statistical analysis of the motion data from motion sensors 11. This statistical analysis may be performed by correlating data from the motion sensors 11 to previous tooth brushing or calibration data, or data stored from other users. For example, after performing the analysis, a certain threshold of correlation of the motion data with previously recorded calibration data that is associated with usage may be determined that indicates brushing has initiated 74 or is in progress. Accordingly, once the user begins brushing, the system 100 may record that usage has been initiated 74 and record the data 76 in memory 14 until usage stops as brushing data, for instance after the correlation falls below a certain threshold. The analysis may utilize a fingerprint or signature type analysis that only compares relative movements. The signature may be determined based on the acceleration in certain axes, as the motion of brushing teeth is generally performed in a relatively rapid motion that is uncharacteristic of any other incidental movement of the toothbrush 1, for example, to put it back in the cabinet. Additionally, the frequency of the brushing may be monitored, as brushing is generally a rapid periodic motion, and therefore various bandpass frequency, low-pass, and Kalman filters may be used or other techniques to identify certain frequencies of interest and amplitudes in those frequencies that indicate brushing. These amplitudes in frequencies may be certain frequencies that reach a threshold amplitude, that are associated or determined to indicate a user is brushing. For example, certain frequencies in horizontal or vertical axes may be required for the system 100 to determine brushing is initiated 74, or certain periodic accelerations that reach certain thresholds may be required for the system to determine brushing has initiated 74. In some embodiments, this may be a frequency of 1-5 Hz. Once the data analyzed by the controller 13 falls below a certain threshold that indicates use, the system 100 may stop recording data or determine that brushing has stopped.

In addition to statistical analysis, the system may detect movement indicating usage or actual brushing by using filtering and threshold analysis. For example, the system 100 may first filter the data from the motion sensors 11 to pass frequencies only in a certain band (as brushing is periodic) and monitor those frequencies to detect when the for one the signal in that reach a threshold for at least a certain number of cycles or duration to determine the user is brushing. For example, if a user brushes their teeth at an average of 1-5 Hz (or potentially less in the case of a motorized toothbrush), a band pass filter of 1-5 Hz may be implemented. Thus when the system 100 detects that amplitude of the frequency band in the 1-5 Hz range reaches a threshold indicating use, the controller 13 may begin to record data from the sensors in the memory 14 for the duration of time the motion data indicates the toothbrush 1 is being used. Additionally, periodic accelerations in certain axes or angular acceleration (for circular brushing) that reaches certain threshold amplitudes may also be used to indicate brushing has initiated. The analysis of the data may also be affected by whether the toothbrush 1 includes an electronic motor to vibrate the head to assist in brushing. In those embodiments, the data may be filtered to eliminate the high frequency acceleration and other noise created by the electronic motor.

In some embodiments, the quality of brushing based of the type of movements the user performs using the toothbrush 1 may be determined. Dentists have indicated that certain movements are more beneficial for brushing, including circular movements, in both clockwise and counterclockwise motions, tip to root motions, and left to right motions. The system 100 may determine if these motions are being performed the relative amount of these motions by filtering the data from motion sensors 11 in certain axes that is indicative of each motion. For example, the data from motions sensors 11 may be filtered in an axis horizontal to gravity, and the controller 13 or other system 100 processors may process the data to determine whether the acceleration, frequency, or other motion data reached a significant enough amplitude in a certain direction to indicate that particular motion is performed. For instance, acceleration alone may be utilized to determine whether back and forth motions are being used, or circular motions. In other embodiments, the acceleration data from motion sensors 11 may be integrated to determine the actual movement of the toothbrush 1 to evaluate the type of brush strokes utilized. The analysis of the data may also be affected by whether the toothbrush 1 includes an electronic motor to vibrate the head to assist in brushing. In those embodiments, the data may be filtered to eliminate the high frequency acceleration and other noise created by the electronic motor.

In some embodiments, an electronic motor to vibrate the head 42 may be included in the toothbrush 1. In those embodiments, the motion data recorded by the sensors relating to brushing movements would have a smaller amplitude than for a manual brush 1. This is because users of manual toothbrushes, without the assistance from the electronic motor and moving head 42, will brush their teeth with more vigorous motions. Accordingly, the algorithms utilized to analyze the motion data to detect, use, motion, and location of toothbrush will be modified to account for the lower amplitudes and/or different motions, and include filtering of the high frequency noise from the motor. Accordingly, in some embodiments, the thresholds set for the amplitude required to detect or indicate a brush stroke would be less, as a user using an electronic toothbrush generally moves the brush at a slower pace, and makes more straight line movements.

Furthermore, pressure sensor 10 may also be utilized to determine whether brushing is actually being performed, or in combination with the motion data from above. For instance, the user may be moving the toothbrush 1 around but not pressing on the teeth. Therefore, accordingly, requiring both motion of a certain frequency, amplitude, or features, and a certain pressure will eliminate many false positives from incidental movement or pressure of the brush that is not happening during brushing. Accordingly, the pressure sensor 10 may output a signal that is analyzed 78 by controller 28 to determine a pressure being applied to the teeth. If the pressure is above a certain threshold, the system 100 may indicate or determine it is likely that a user is brushing. This analysis may be performed by statistical analysis, threshold analysis or other suitable calculation methods for determining a likelihood of brushing based on the amount and/or sustained nature of the pressure recorded by pressure sensor 10.

Usage Monitor for Replaceable Heads

Additionally, the total number of uses for a replaceable toothbrush 1 head 42 may be detected and stored in the memory 13 of the toothbrush 1 or associated with the server 4, to monitor the useful life of a single toothbrush 1 head 42. Thus, the system 100 could provide a notification to the user, for example on their mobile device 30 or through the webpage interface to the sever 4, once a particular toothbrush 1 head 42 has been used a certain number or duration of time. Once a head 42 has been exhausted, the user will disconnect and reconnect a new head 42, which could be interpreted or recorded by the system 100 as attaching a new toothbrush 1. Additionally, each head 42 may incorporate a unique identity module that stores an identifier for that specific head 42, so when the same head 42 is reattached, for example, for cleaning or other purposes, the system 100 will not assume a new head 42 has been attached.

Brushing Time and Position

Next, the brushing data recorded above may be analyzed 78 to provide feedback on the positional and time quality of brushing 80. This may be presented after brushing has completed or in real time to provide instantaneous feedback to the user. For example, the motion sensors 11 may detect positional information of the toothbrush 1. Using the accelerometer and gyroscope data or other motion sensors 11, the position, orientation, and movement of the toothbrush 1 may be determined and extrapolated to calculate the relative positional movement of the head 42. For instance, if the distance, orientation, and direction of the motion sensors 11 to the bristle portion of the head 42 are known, the system 100 will be able to determine the position of the head 42, and its relative motion, orientation, and coverage area based on the relative motion of the motion sensors 11. This may be calculated by initially calculating a reference coordinate once the toothbrush 1 detects motion, and recording the relative movement with respect to the initial coordinate(s) to determine a signature of the brushing. This may be performed by calculating the movement of the head 42 by calculating the changes in orientation of the brush and the movement due to acceleration recorded by the gyroscope or accelerometer. These calculations may be performed by the controller 13, or other processors that are utilized in the system 100, including a mobile phone processor executing an application on the mobile phone, or a processor(s) on a server running software for analyzing the data.

In order to utilize the data from the sensors to estimate the amount of time spent in each section, quadrant or other logical division of the mouth, the user may need to calibrate the toothbrush 1. For example, in some embodiments, the user may apply a colored gel to their teeth. The user can then turn the toothbrush 1 in calibration mode once the toothbrush 1 is in position in by the teeth and brush away all of the colored gel, while the motion sensors 11 and other sensors are recording data. At this point, the user may switch off calibration to stop the acquisition of calibration data. In other embodiments, once the user turns on the calibration function, the toothbrush 1 would detect the points in time when the user has started and stopped brushing, including any pauses in the brushing. This calibration procedure provides reference positional, orientation, and motion calibration data that can then be compared to subsequent brushes using statistical analysis 78, or other analysis methods to determine whether subsequent brushes have brushed all regions of the mouth for sufficient time.

Once the device is calibrated, or using reference data from previous brushing or and other model users brushing, brushing data from each usage may be compared to reference data to evaluate its quality 78 and determine the position of the toothbrush 1 in the newly acquired data. For instance the calibration data may be utilized to prepare a statistical model of the shape and dimensions of a specific user's mouth and be used to create certain statistical boundaries for determining when the toothbrush 1 is brushing any certain section of the user's mouth. Then, once a user initiates brushing a second time, the newly recorded data could then be overlaid or correlated with the calibration brushing data associated with that user profile, to determine whether and where there were any deficiencies in the brushing. For instance, the system 100 may determine how much time is spent brushing each quadrant, how many strokes, or perform other evaluations of the brushing. Additionally, the analysis may indicate that a user brushed too much in certain areas or did not use the correct stroke patterns generally or in specific sections of the user's mouth.

The correlation may be performed by statistical analysis, for example, a quantitative comparison of such differences can be made simply by measuring the Euclidean distance in the 3xz space. Such vectors may then be treated by using statistical analyses, including principal component analysis (PCA), hierarchical cluster analysis (HCA), regression analysis, and linear discriminant analysis. Statistical methods suitable for high dimensionality data may be utilized. As an example, HCA systematically examines the distance between the data that represent each type of motion or positional data. A dendrogram can then be generated that shows the clustering of the data from the Euclidean distances between and among the data vectors, much like an ancestral tree.

Each statistical data cluster may be representative of sensor data for each section, quadrant or other logical division of the user's mouth. For example, the mouth may be divided into, top and bottom, with top and bottom each having a right front and left portion, and each of the right, front and left portions, having an inside, top, and outside face. Accordingly, the mouth may have 36 different sections, 10 sections, 8 sections, 12 sections, or 4 sections (quadrants), top and bottom only, outer and inner only, and other logical divisions. Accordingly, using reference data, the controller 13, or other processors in the system 100 (e.g., processors in the mobile phone or servers), may calculate the confidence interval or other value indicating the likelihood the toothbrush is brushing a specific section of the user's mouth, but determine the likelihood the strokes correlate or relate to the calibration data in those sections. In order to acquire a reference position, the user may be instructed to initiate brushing at an identical position of the mouth. That way, the data starts at a known position and can use that as a reference point to relate the rest of the data using statistical analysis. For instance, the angle, orientation, calculated distance and other features from the reference position of the toothbrush 1 detected by the motion sensor 11 may indicate the likelihood each new position is correlated to a certain position of the mouth based on calibration data.

In other embodiments, the controller 13 or other system processors (e.g. processors in the smartphone, servers, or other components) may process the statistical data and determine that the brush is brushing a certain section of the mouth if the statistical analysis shows with great than 95%, 85%, 80% or other suitable certainty that the brush is within the section of the mouth. In some embodiments, the specificity or sensitivity of the brushing statically analysis may be modified to match a specific user's variance.

This analysis may include an output 80 that allows the controller 13 or other processors to determine which brush strokes were in each section of the mouth or tooth set, and therefore how much time a user spend brushing each quadrant, half or tooth, or other logical division of the mouth and how those times compare to recommended regimes. In other embodiments, the time at the beginning and end of entering a certain area may be recorded, or other suitable methods to determine how much time is spent brushing each section of the mouth.

In some embodiments, rather than detect the position of the toothbrush, the system 100 may direct the user to brush certain sections of the mouth one at a time, and only determine whether or not the user is actually brushing, and count or record brushing time only while motion indicative of brushing is detected. Then, once brushing has been recorded in the directed section for the prescribed time, the system 100 would indicate to the user that it is time to move to the next section of the mouth, and elapse time when the user is actually brushing. This prevents the user from taking breaks and thereby brushing for less than the optimal amount of time in each section. Accordingly, the controller 13 or other processors may analyze the data from the sensors 11 (or pressure sensor 10) to record the amount of time the user was brushing in each section while the system 100 indicated the user should be brushing in that particular section.

In other embodiments, pressure exerted on the head 42 from brushing may also be detected by a pressure sensor 10 incorporated into toothbrush 1. For example, the pressure sensor 10 may be incorporated into the head 42, and detect a pressure associated with usage. Additionally, the pressure may be mapped to the various positional data and therefore the controllers 13 or other processors of the system 100 may calculate the amount of pressure utilized for brushing each area of the mouth.

Presentation of Feedback

Once the system's 100 controller(s) 13, or other processors contained in the smartphone, servers, or other components of the system 100 have analyzed the usage data 78, feedback may be presented to the user 80 through the speaker 50, the visual indicators 52 on the toothbrush 1, or through an associated mobile device 30 or other computing device in data communication with the system 100. This feedback may be presented instantaneously or available for access to check progress.

For instance, instantaneous feedback may be provided to the user 80 during brushing, that includes indications by audio or visual means that indicate how much time is left, whether to brush harder or softer, whether certain quadrants have been sufficiently brushed, and when brushing is completed. For example, a red light or stop sound may be produced through the speaker 50 to indicate the brushing is completed.

Additionally, historic and average brushing times and positional data may be presented to the user 80 on the mobile device or other computing device using graphs, charts, percentages and other metrics. For instance, the user could be presented with the average time spent per day, per quadrant, and the average days the user brushes once, twice or other times. Additionally, the average time spent brushing per tooth may be calculated and presented to the user on the mobile device 30 or other computing device. A program 15 running on the mobile device may control the presentation of the data, using the mobile device 30 controller 13.

API for Dentist Integration

An API may also be developed for transferring the brushing and usage data to a dentist for professional evaluation and feedback on brushing habits and techniques. Furthermore this data may be evaluated to determine brushing techniques that result in more dental issues, including cavities and gum disease. For instance, the width or height of the strokes may be correlated to how high along the gum-line the brush reaches, indicating whether the gums are properly brushed. This could be analyzed to determine whether short strokes in height lead to more frequent instances of gum disease.

Gamification

The usage data may also be used to create games for children or family members to play alone or against each other, to hit certain thresholds of usage. This can provide a unique motivational tool for users to brush their teeth on a regular basis. Accordingly, as delayed feedback, for example, in the case of gum disease or cavities generally is discounted psychologically, the more immediate and continual concrete, and quantitative feedback of the present disclosure will provide a much better incentive to conform to recommend brushing regimens.

The invention claimed is:

1. An electronic toothbrush system for monitoring brushing and compliance with a toothbrush regime, the electronic toothbrush system comprising:
   a toothbrush including a handle and a head;
   a motion sensor configured to output motion data related to motion of the toothbrush;
   a memory for storing the motion data output by the motion sensor; and
   a statistical analyzer configured to determine a likelihood that the head of the toothbrush is positioned in a particular one of a plurality of sections of a mouth of a user by comparing the motion data to previously recorded calibration data using statistical analysis, the statistical analysis including determining Euclidean distances between a first data point of the motion data and a plurality of data points of the calibration data.

2. The electronic toothbrush system of claim 1, further comprising a controller for calculating the time elapsed brushing a particular one of the plurality of sections of the mouth of the user.

3. The electronic toothbrush system of claim 2, wherein the controller is configured to determine when the user has sufficiently brushed the particular one of the plurality of sections of the mouth of the user.

4. The electronic toothbrush system of claim 1, wherein the memory is configured to store the motion data output from the motion sensor responsive to a brushing session beginning.

5. The electronic toothbrush system of claim 1, wherein the motion sensor is incorporated in the toothbrush and the motion data includes acceleration data.

6. The electronic toothbrush system of claim 1, wherein the motion data includes orientation data.

7. The electronic toothbrush system of claim 1, wherein the statistical analyzer filters motion data using a band pass filter.

8. The electronic toothbrush system of claim 1, wherein the statistical analysis is a regression analysis.

9. The electronic toothbrush system of claim 1, wherein the statistical analysis is performed using a known starting position in the mouth of the user.

10. The electronic toothbrush system of claim 1, wherein the statistical analysis is performed by fitting the motion data to the calibration data after the system determines brushing has stopped.

11. The electronic toothbrush system of claim 1, wherein the system presents feedback to the user regarding the amount of time spent brushing each of the plurality of sections of the mouth of the user.

12. The electronic toothbrush system of claim 1, wherein each of the plurality of data points of the calibration data is associated with a position of the head of the toothbrush in the mouth of the user during a calibration session.

13. The electronic toothbrush system of claim 12, wherein each of the plurality of data points of the calibration data is also associated with a brushstroke pattern of the head of the toothbrush during the calibration session.

14. The electronic toothbrush system of claim 13, wherein the brushstroke pattern of the head of the toothbrush is a clockwise circular brushstroke pattern, a counterclockwise circular brushstroke pattern, a tip to root brushstroke pattern, or a back-and-forth brushstroke pattern.

15. The electronic toothbrush system of claim 1, wherein the statistical analysis includes a principal component analysis, a hierarchical cluster analysis, a regression analysis, or a linear discriminate analysis.

16. The electronic toothbrush system of claim 1, wherein the statistical analysis includes systematically examining the Euclidean distances using a hierarchical cluster analysis.

17. The electronic toothbrush system of claim 16, wherein the statistical analysis includes generating a dendrogram showing statistical data clusters determined from the Euclidean distances.

18. The electronic toothbrush system of claim 17, wherein each of the statistical data clusters are representative of one of the plurality of sections of the mouth of the user.

19. An electronic toothbrush system for monitoring brushing and compliance with a toothbrush regime, the electronic toothbrush system comprising:
  a toothbrush including a handle and a head;
  a motion sensor configured to output motion data related to motion of the head of the toothbrush; and
  a controller including a memory device and one or more processors, the controller being configured to
    (i) determine a Euclidean distance between a first data point of the motion data and a plurality of data points of previously recorded calibration data, each of the plurality of data points of previously recorded calibration data being associated with a position of the head of the toothbrush in a mouth of a user during a calibration session, and
    (ii) based on the Euclidean distance between the first data point of the motion data and the plurality of data points of previously recorded calibration data, determine a current position of the head of the toothbrush in the mouth of the user using statistical analysis.

20. The electronic toothbrush system of claim 19, wherein the statistical analysis includes a principal component analysis, a hierarchical cluster analysis, a regression analysis, or a linear discriminate analysis.

21. The electronic toothbrush system of claim 19, wherein each of the plurality of data points of previously recorded calibration data is associated with a brushstroke pattern, and the controller is configured to determine, based on the Euclidean distance between the first data point of the motion data and the plurality of data points of previously recorded calibration data, a brushstroke pattern of the head of the toothbrush.

22. The electronic toothbrush system of claim 21, wherein the brushstroke pattern of the head of the toothbrush is a clockwise circular brushstroke pattern, a counterclockwise circular brushstroke pattern, a tip to root brushstroke pattern, or a back-and-forth brushstroke pattern.

23. The electronic toothbrush system of claim 19, further comprising a pressure sensor configured to output pressure data related to a force applied on the toothbrush and wherein the controller is configured to determine that the head of the toothbrush is applied to one or more teeth in the mouth of the user by comparing the stored pressure data with a threshold pressure value, thereby indicating a beginning of a first portion of a brushing session.

* * * * *